(12) United States Patent
Ganzer (10) Patent No.: US 10,806,920 B2
(45) Date of Patent: Oct. 20, 2020

(54) NON-INVASIVE AND SELECTIVE BIOELECTRONIC CONTROL OF BLOOD PRESSURE

(71) Applicant: Battelle Memorial Institute, Columbus, OH (US)

(72) Inventor: Patrick Ganzer, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

(21) Appl. No.: 16/577,080

(22) Filed: Sep. 20, 2019

(65) Prior Publication Data

US 2020/0094040 A1  Mar. 26, 2020

Related U.S. Application Data

(60) Provisional application No. 62/734,670, filed on Sep. 21, 2018.

(51) Int. Cl.
*A61N 1/36* (2006.01)
*A61N 1/04* (2006.01)

(52) U.S. Cl.
CPC ........ *A61N 1/0456* (2013.01); *A61N 1/36031* (2017.08); *A61N 1/36034* (2017.08)

(58) Field of Classification Search
CPC .............. A61N 1/0456; A61N 1/36031; A61N 1/36034; A61N 1/0404; A61N 1/36014; A61B 5/021; A61B 5/4836
See application file for complete search history.

(56) References Cited

U.S. PATENT DOCUMENTS

| | | | |
|---|---|---|---|
| 3,650,277 | A | 3/1972 | Sjostrand |
| 6,450,942 | B1 | 9/2002 | Lapanashvili et al. |
| 6,681,136 | B2 | 1/2004 | Schuler et al. |
| 6,832,982 | B1 | 12/2004 | Lapanashvili et al. |
| 6,957,106 | B2 | 10/2005 | Schuler et al. |
| 7,373,204 | B2 | 5/2008 | Gelfand et al. |
| 7,725,188 | B2 | 5/2010 | Errico et al. |
| 7,835,797 | B2 | 11/2010 | Rossing et al. |
| 7,869,879 | B2 | 1/2011 | Errico et al. |

(Continued)

FOREIGN PATENT DOCUMENTS

| | | |
|---|---|---|
| EP | 0323052 A2 | 7/1989 |
| EP | 0645162 A1 | 3/1995 |

OTHER PUBLICATIONS

He W, Wang X, Shi H, Shang H, Li L, Jing X, Zhu B. (2012) Auricular acupuncture and vagal regulation. Evid Based Complement Alternat Med. 2012:786839.

(Continued)

*Primary Examiner* — George Manuel
(74) *Attorney, Agent, or Firm* — Pearne & Gordon LLP (57) ABSTRACT

Methods and systems for non-invasive selective control of blood pressure are described. For example, noninvasive stimulation of the auriculotemporal nerve (on the surface of the ear) facilitates a decrease in blood pressure without a corresponding decrease in heart rate or breathing rate, as occurs in stimulation of the cervical vagus and trigeminal nerves. Such a therapy may be particularly beneficial during hypertensive crises or like events where the body naturally decreases heart rate and breathing rate to compensate for an increased blood pressure.

20 Claims, 11 Drawing Sheets

(56) References Cited

U.S. PATENT DOCUMENTS

| | | | |
|---|---|---|---|
| 7,873,413 B2 | 1/2011 | McCabe et al. | |
| 7,904,159 B2 | 3/2011 | Errico et al. | |
| 8,740,825 B2 | 6/2014 | Ehrenreich et al. | |
| 8,747,338 B2 | 6/2014 | Ehrenreich et al. | |
| 8,755,892 B2 * | 6/2014 | Amurthur | A61B 5/021 607/136 |
| 8,768,469 B2 | 7/2014 | Tweden et al. | |
| 8,843,210 B2 | 9/2014 | Simon et al. | |
| 8,918,178 B2 | 12/2014 | Simon et al. | |
| 8,983,628 B2 | 3/2015 | Simon et al. | |
| 8,983,629 B2 | 3/2015 | Simon et al. | |
| 9,002,458 B2 | 4/2015 | Pal et al. | |
| 9,011,355 B2 | 4/2015 | Ehrenreich et al. | |
| 9,014,811 B2 | 4/2015 | Pal et al. | |
| 9,031,650 B2 | 5/2015 | McCabe et al. | |
| 9,089,691 B2 | 7/2015 | Libbus et al. | |
| 9,095,711 B2 | 8/2015 | Tweden et al. | |
| 9,233,244 B2 | 1/2016 | Pal et al. | |
| 9,358,381 B2 | 6/2016 | Simon et al. | |
| 9,399,134 B2 | 7/2016 | Simon et al. | |
| 9,415,219 B2 | 8/2016 | Simon et al. | |
| 9,415,220 B1 | 8/2016 | Spinelli et al. | |
| 9,616,231 B2 | 4/2017 | Tweden et al. | |
| 9,623,240 B2 | 4/2017 | Simon et al. | |
| 2005/0090867 A1 | 4/2005 | Lapanashvili et al. | |
| 2006/0122675 A1 | 6/2006 | Libbus et al. | |
| 2008/0015659 A1 | 1/2008 | Zhang et al. | |
| 2008/0288016 A1 | 11/2008 | Amurthur et al. | |
| 2009/0287035 A1 | 11/2009 | Dietrich et al. | |
| 2011/0202107 A1 | 8/2011 | Sunagawa et al. | |
| 2013/0102937 A1 | 4/2013 | Ehrenreich et al. | |
| 2014/0288472 A1 | 9/2014 | Ehrenreich et al. | |
| 2015/0190307 A1 | 7/2015 | Ehrenreich et al. | |
| 2015/0238766 A1 | 8/2015 | McCabe et al. | |
| 2016/0279410 A1 | 9/2016 | Simon et al. | |

OTHER PUBLICATIONS

Ganzer PD, Darrow MJ, Meyers EC, Solorzano B, Robertson N, Adcock K, James J, Ruiz A, Jeong HS, Becker A, Goldberg MP, Pruitt D, Hays SA, Kilgard MP, Rennaker RL 2nd (2018) Closed-loop Neuromodulation Restores Network Connectivity and Motor Control after Spinal Cord Injury. eLife. 7. pii: e32058.
Shqau K and Heintz A (2017) Mixed Ionic Electronic Conductors for Improved Charge Transport in Electrotherapeutic Devices. Paper No. DMD2017-3454, pp. V007T0A003; 2 page doi:10:1115/DMD2017-3454.
Birmingham K, Gradinaru V, Anikeeva P, Grill WM, Pikov V, McLaughlin B, Pasricha P, Weber D, Ludwig K, Famm K. (2014) Bioelectronic medicines: a research roadmap. Nat Rev Drug Discov. 13(6):399-400. doi: 10.1038/nrd4351.
Guiraud D, Andreu D, Bonnet S, Carrault G, Couderc P, Hagège A, Henry C, Hernandez A, Karam N, Le Rolle V, Mabo P, Maciejasz P, Malbert CH, Marijon E, Maubert S, Picq C, Rossel O, Bonnet JL. (2016) Vagus nerve stimulation: state of the art of stimulation and recording strategies to address autonomic function neuromodulation. J Neural Eng. Aug. 2013;13(4):041002. doi: 10.1088/1741-2560/13/04/041002.
Meyers EC, Solorzano BR, James J, Ganzer PD, Lai E, Rennaker Rl II, Kilgard MP, and Hays SA (2018) Vagus nerve stimulation enhances stable plasticity and generalization of stroke recovery. Stroke. pii:STROKEAHA.117.019202.
Ganzer PD, Beringer CR, Shumsky JS, Nwaobasi C, Moxon KA. (2018b) Serotonin receptor and denritic plasticity in the spinal cord mediated by chronic serotonergic pharmacotherapy combined with exercise following complete SCI in the adult rat. Exp Neurol. 304:132-142.
Manohar A, Foffani G, Ganzer PD, Bethea J, Moxon KA (2017) Cortex dependent recovery of unassisted hundlimb locomotion after complete spinal cord injury in the adult rat. Elife. 6. pii: e23532.
Hays SA (2016) Enhancing Rehabilitative Therapies with Vagus Nerve Simulation. Neurotherapeutics. 13(2):382-94. doi: 10.1007/s13311-015-0417-z.
Khodaparast N, Kilgard MP, Casavat R, Ruiz A, Qureshi Iqra, Ganzer PD, Rennaker RL 2nd, Hays SA (2015) Vagus Nerve Stimulation during Rehabilitative Training Improves Forelimb Recovery after Chronic Ischemic Stroke in Rats. Neurorehabilitation and Neural Repair.
He K, Huertas M, Hong SZ, Tie X, Hell JW, Shouval H, Kirkwood A (2015) Distinct Eligibility Traces for LTP and LTD in Cortical Synapses. Neuron. 88(3):528-38. doi: 10.1016/j.neuron.2015.09.037.
Mercante B, Deriu F, Rangon CM. (2018) Auricular Neuromodulation: The Emerging Concept beyond the Stimulation of Vagus and Trigeminal Nerves. Medicines (Basel). 5(1). pii: E10. doi: 10.3390/medicines5010010.
Bouton CE, Shaikhouni A, Annetta NV, Bockbrader MA, Friedenberg DA, Nielson DM, Sharma G, Sederberg PB, Glenn BC, Mysiw WJ, Morgan AG, Deogaonkar M, Rezai AR. Restoring cortical control of functional movement in a human with quadriplegia. Nature. May 12, 2016;533(7602):247-50. doi: 10.1038/nature17435. Epub Apr. 13, 2016.
Chowhurdy T, Mendelowith D, Golanov E, Spiriev T, Arasho B, Sandu N, Sadr-Eshkevari P, Meuwly C, Schaller B (2015) Trigeminocardiac reflex: the current clinical and physiological knowledge. J Neurosurg Anesthesiol. 27(2):136-47.
Wehrwein EA, Joyner MJ (2013) Regulation of blood pressure by the arterial baroreflex and autonomic nervous system. Handb Clin Neurol. 117:89-102. Coleman TG (1980) Arterial Baroreflex control of heart rate in the conscious rat. Am J Physiol. 238(4):H515-20.
Plachta DT, Gierthmeuhlen M, Cota O, Boeser F, Stieglitz T. (2013) BaroLoop: using a multichannel cuff electrod and selective stimulation to reduce blood pressure. Conf Proc IEEE Eng Med Biol Soc. 2013:755-8. doi: 10..1109/EMBC.2013.6609610.
Plachta DT, Gierthmuehlen M, Cota O, Espinosa N, Boeser F, Herrera TC, Stieglitz T, Zentner J (2014) Blood pressure control with selective vagal nerve stimulation and minimal side effects. J. Neural Eng. 11(3):036011.
Plachta DT, Zentner J, Aguire D, Cota O, Stieglitz T, Gierthmuehlen M (2016) Effect of Cardiac-Cycle Synchornized Selective Vagal Stimulation on Heart Rate and BloodPressure in Rats. Adv Ther. 33(7):1246-61.
Kim Y, Kanneganti A, Nothnagle C, Landrith R, Mizuno M, Wijesundara MBJ, Smith S, and Romero-Ortega MI (2015) Microchannel Electrode Stimulation of Deep Peroneal Nerve Fascicles Induces Mean Arterial Depressor Response in Hypertensive Rats. Bioelectron Med. 2:55-62.
Head GA (1994) Cardiac baroreflexes and hypertension. Clin Exp Pharmacol Physiol. 21(10):791-802.
Reid IA (1992) Interactions between ANG II, sympathetic nervous system, and baroreceptor reflexes in regulation of blood pressure. Am J Physiol. 262(6 Pt 1):E763-78.
International Search Report and Written Opinion issued in corresponding International PCT Application No. PCT/US2019/052070; dated Nov. 29, 2019.
Coleman; Arterial baroreflex control of heart rate in the conscious rat; American Physiological Society; 2980; downloaded from www.physiology.org/hournal/ajpheart Aug. 2018.

* cited by examiner

FIGURE 5A
cVNS

FIGURE 5B
atNS

FIGURE 6A
cVNS

FIGURE 6B
atNS

FIGURE 7A
cVNS

FIGURE 7B
atNS

NON-INVASIVE AND SELECTIVE BIOELECTRONIC CONTROL OF BLOOD PRESSURE

CROSS-REFERENCE TO RELATED APPLICATIONS

This application claims priority to U.S. Provisional Application Ser. No. 62/734,670, filed on Sep. 21, 2018, entitled "NON-INVASIVE AND SELECTIVE BIOELECTRONIC CONTROL OF BLOOD PRESSURE", the entirety of which is incorporated herein by reference.

BACKGROUND OF THE INVENTION

Bioelectronic medicine is a field of therapeutics aimed at treating dysfunction and disease using peripheral nerve stimulation. Nerve stimulation is generally used as way to affect molecule release, organ function, central nervous system activity, and other physiological events. Particularly, Vagus nerve stimulation (VNS) is one of the most common bioelectronic medicine interfaces and has been used to treat a wide array of diseases including epilepsy, depression, heart failure, and obesity.

Bioelectronic VNS protocols generally follow a preprogrammed nerve stimulation schedule, otherwise known as open-loop stimulation. For example, open-loop VNS treatments for patients suffering from epilepsy may follow a preprogrammed schedule delivering stimulation throughout the day at a 30 second duty cycle followed by 5 minutes without stimulation.

Some disease states may benefit from closed-loop stimulation to trigger rapid neural activation and optimized therapeutic effects. For example, spinal cord injury (SCI) and stroke are leading causes of paralysis, and commonly leave motor circuits extensively damaged (e.g. neural circuits innervating the musculature of a limb). These damaged circuits can be rewired to enable recovery using therapies that promote neural circuit change, otherwise known as neural plasticity (e.g. synaptic plasticity or axonal sprouting). Closed-loop bioelectronic medicines can facilitate neural plasticity and recovery following injury.

Bioelectronic stimulation may be non-invasive by targeting nerve branches that are accessible via transcutaneous stimulation. However, there remain challenges facing non-invasive bioelectronic medicines. These include, for example, the identification of a sufficiently robust electrode material for stimulation. Further, invasive stimulation may directly target a nerve (or nerve branch) of interest to provide a particular physiological function, for example with a cuff electrode placed directly on the nerve. In contrast, non-invasive stimulation may be less selective of nerve activation or physiological function.

BRIEF SUMMARY OF THE INVENTION

According to one example, a method of the present disclosure comprises non-invasively stimulating a surface of an outer ear or an auriculotemporal nerve of a subject such that: a blood pressure of the subject decreases relative to the blood pressure at the time stimulation is applied; and concomitantly with the decrease in blood pressure: a heart rate of the subject is maintained or increased, or the heart rate of the subject increases more than in response to said stimulation applied to the cervical vagus or trigeminal nerve.

In various embodiments of the above example, the stimulation is applied at an area of the outer ear innervated by the auriculotemporal nerve of the subject; the stimulation is applied with an electrode comprising a mixed ionic electronic conducting electrode interface; the applied stimulation is of at least 40 microcoulombs; the applied stimulation comprises pulses of less than or equal to 3 mA at less than or equal to 100 Hz, each pulse having a pulse width less than or equal to 0.9 ms for a pulse train less than or equal to 15 minutes; each pulse is a biphasic square wave having an anodal leading edge; the stimulation is applied during a hypertensive crisis; and/or a parameter of the stimulation or a time of application of the stimulation is determined based on a detected physiological parameter.

According to a second example of the disclosure herein, a method of decreasing a blood pressure of a subject comprises stimulating a surface of an outer ear or an auriculotemporal nerve of a subject with at least 40 microcoulombs, thereby concomitantly decreasing said blood pressure and maintaining or increasing a heart rate of said subject during said stimulation.

In various embodiments of the second example, the stimulation is applied at an area of the outer ear innervated by the auriculotemporal nerve of the subject; the stimulation is applied with an electrode comprising a mixed ionic electronic conducting electrode interface; the stimulation comprises electrical pulses of less than or equal to 3 mA at less than or equal to 100 Hz, each pulse having a pulse width less than or equal to 0.9 ms for a pulse train less than or equal to 15 minutes; each pulse is a biphasic square wave having an anodal leading edge; and/or a parameter of the stimulation or a time of application of the stimulation is determined based on a detected physiological parameter.

In still other examples of the present disclosure, a stimulation device can be used to perform any of the above methods. For example, a stimulation device may comprise: a power source; and an electrode configured to apply a stimulation current to a surface of an outer ear of a subject, the stimulation current being supplied by the power source, wherein: the stimulation current applies at least 40 microcoulombs, and a blood pressure of the subject is decreased concomitantly with a maintenance or increase in a heart rate of the subject, in response to said application of the stimulation current.

In various embodiments of the above example, the stimulation current comprises pulses of less than or equal to 3 mA at less than or equal to 100 Hz, each pulse having a pulse width less than or equal to 0.9 ms for a pulse train less than or equal to 15 minutes; each pulse is a biphasic square wave having an anodal leading edge; the electrode comprises a mixed ionic electronic conducting electrode interface; the system further comprises a controller; and a physiological sensor configured to detect a physiological parameter of the subject, wherein the controller is configured to determine a parameter of the stimulation current or a time of application of the stimulation current, and to correspondingly control the power source to supply the stimulation current to the electrode, based on the detected physiological parameter; and/or the controller is configured to cause said application of the stimulation current during a hypertensive crisis.

DETAILED DESCRIPTION OF THE INVENTION

Currently, it is believed that stimulation of the left cervical branch of the vagus nerve activates ascending aortic baroreceptor fibers (mediating vasodilation) as well as descending cardiac sinoatrial fibers (mediating bradycardia). Thus, cervical Vagus nerve stimulation (cVNS) sufficient to induce a response can cause a decrease in blood pressure but also causes a corresponding slowing of the heart rate. A decrease in breathing rate (bradypnea) has also been found with cVNS.

Figure 1:
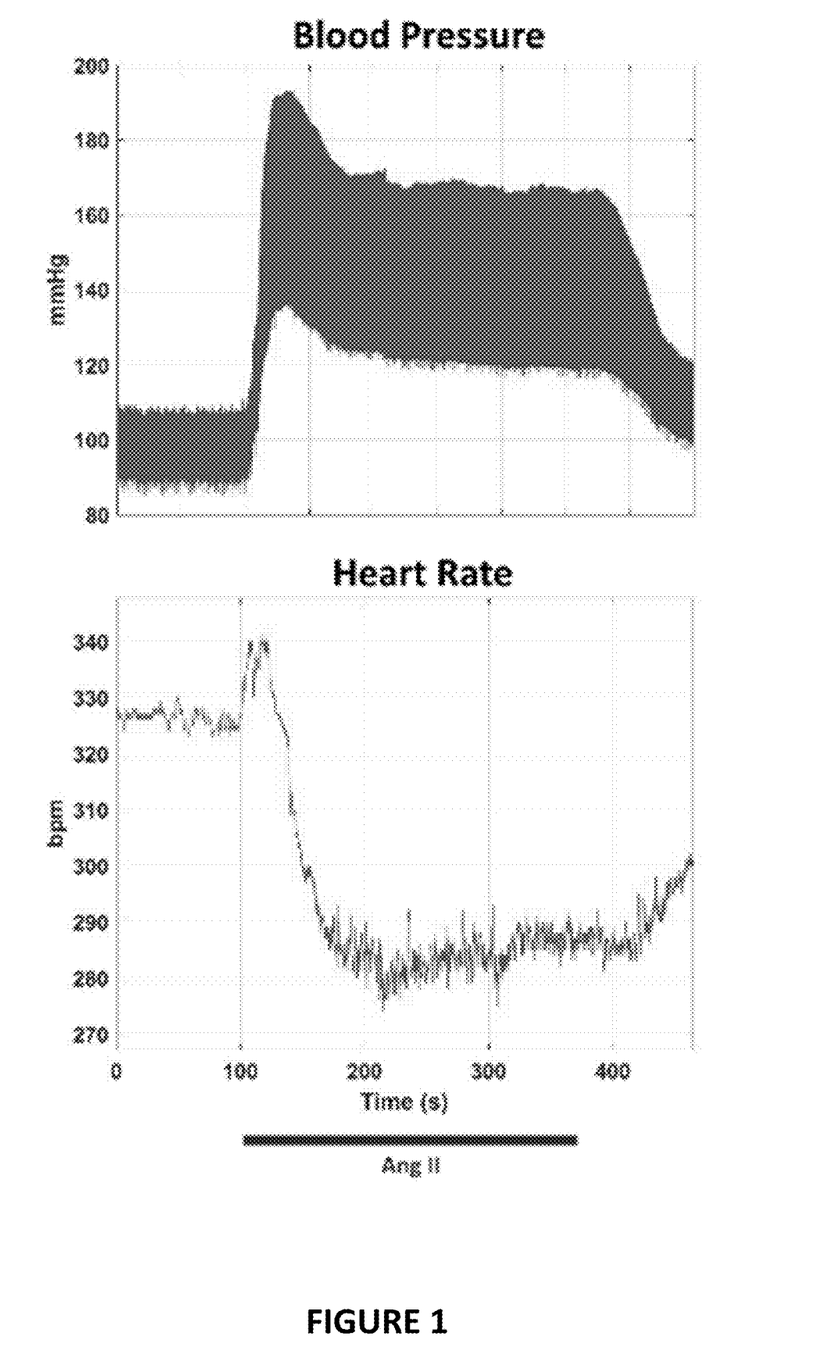
FIG. 1 illustrates the reflective decrease in heart rate in response to increased blood pressure induced by an Angiotensin II application.

However, when treating hypertension, it would be desirable to avoid exacerbating bradycardia and bradypnea during hypertensive events. This is because the body commonly attempts to decrease blood flow during high blood pressure states via 'reflexive' slowing of the heart and breathing. This type of response is illustrated in FIG. 1. As seen therein, a hypertensive crisis was induced with the application of Angiontensin II (Ang II) via injection. As measured blood pressure increased in response to the Ang II application, heart rate decreased followed by a slow decrease in blood pressure toward the resting level. This lasted until Ang II application was stopped. In view of this, if a therapy for treating high blood pressure during a hypertensive event further causes bradycardia and bradypnea, the therapy can exacerbate the naturally decreased heart rate and breathing rate.

In view of the above, the present disclosure relates to non-invasive bioelectronic stimulation; and particularly, for selective control of blood pressure (e.g., arterial blood pressure (ABP)) in a manner that does not also affect heart rate or breathing rate. Such control may thus represent a bioelectronic therapeutic for treating hypertensive states. Selective control of blood pressure (e.g., decreased blood pressure without corresponding decreases in heart rate and/or breath rate) can be useful in other similar physiological states, diseases, and therapeutic scenarios other than hypertension. For example, treatments of coronary artery disease, arrhythmias, atherosclerosis, pericarditis, myocarditis, obstructive shock, stroke, intracerebral pressure and edema, and the like can also benefit from the bioelectronic control of the present disclosure.

More particularly, auriculotemporal nerve stimulation (atNS) can selectively lower blood pressure without a corresponding decrease in heart rate. The auriculotemporal nerve is a small component of the mandibular branch of the trigeminal nerve. The auriculotemporal nerve is mainly composed of afferent fibers from the gasserian ganglion near the temporomandibular joint. It is believed that atNS causes activation of a subcomponent of the trigeminocardiac reflex (TCR). Mechanical compression of many branches of the trigeminal nerve seems to mediate pronounced hypotension and/or bradycardia. It is further believed that atNS activates classic 'baroreflex circuits' without activating heart beat regulating circuits. This is because a subset of the baroreflex circuitry takes inputs from the periphery or vasculature, and in turn inhibits vasoconstriction via descending input to neurons in the spinal cord, leading to vasodilation.

Figure 2:
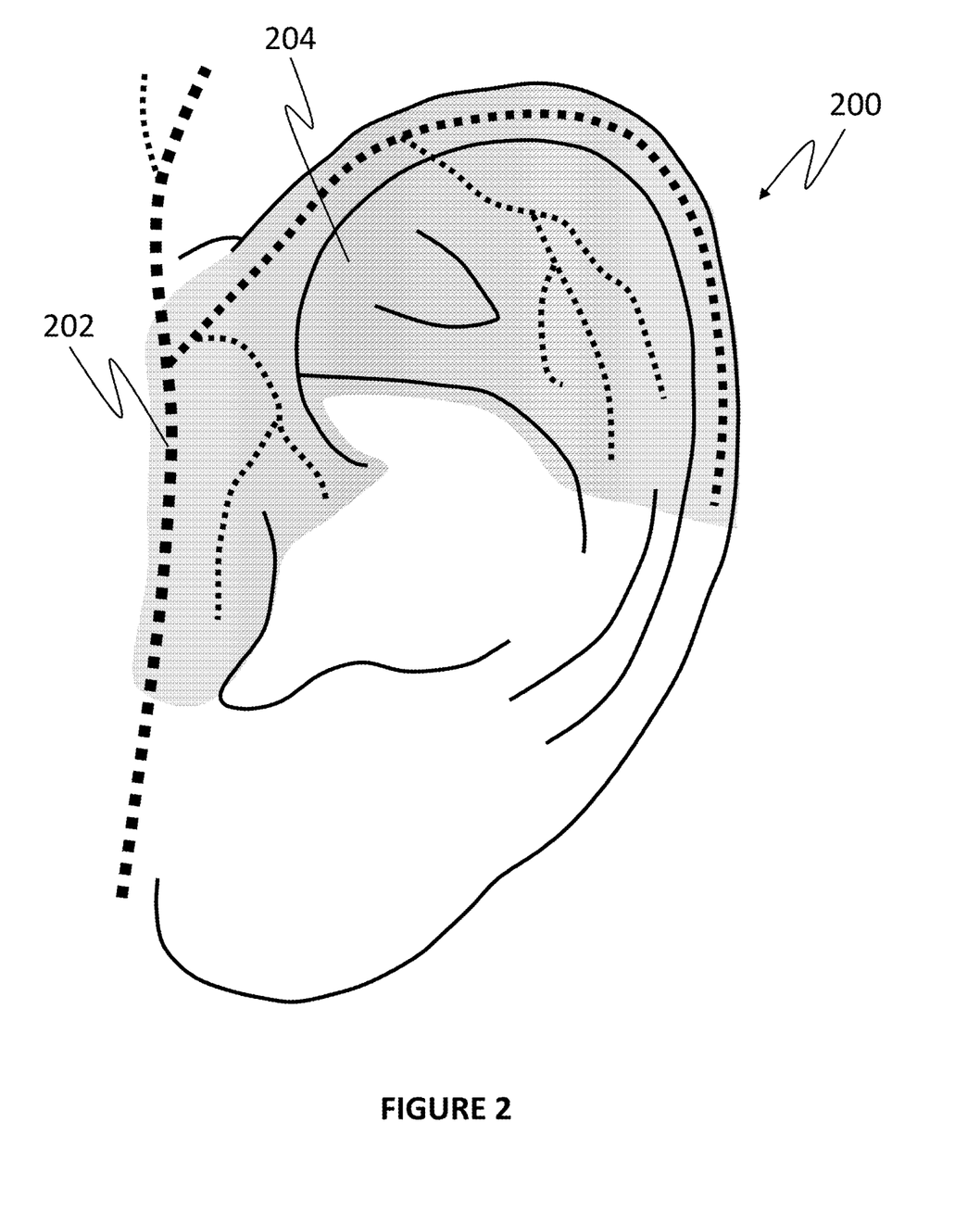
FIG. 2 illustrates the auriculotemporal innervation of the outer ear.

The auriculotemporal nerve may be non-invasively activated most effectively by stimulation at a site on the outer ear corresponding to the auriculotemporal nerve's innervation of the outer ear. FIG. 2 illustrates this anatomical innervation. Notably, the auriculotemporal nerve 202 is accessible in a region 204 of the outer ear 200 near the area surrounding the concha particularly the antihelix. Although not shown, it is also noted that the outer ear 200 ear includes the auricular branch of the vagus nerve (accessible from near the tragus and concha), the occipital nerve (accessible from near the helix and antihelix), and the greater auricular nerve (accessible from around the lobule). Accordingly, a further aspect of the present disclosure relates to non-invasive transcutaneous stimulation at an area of the outer ear surrounding the concha, particularly including portions of the antihelix to selectively decrease blood pressure without a decrease or other significant change to heart rate. Such stimulation is hereinafter referred to as non-invasive auriculotemporal nerve stimulation (atNS).

Figure 3:
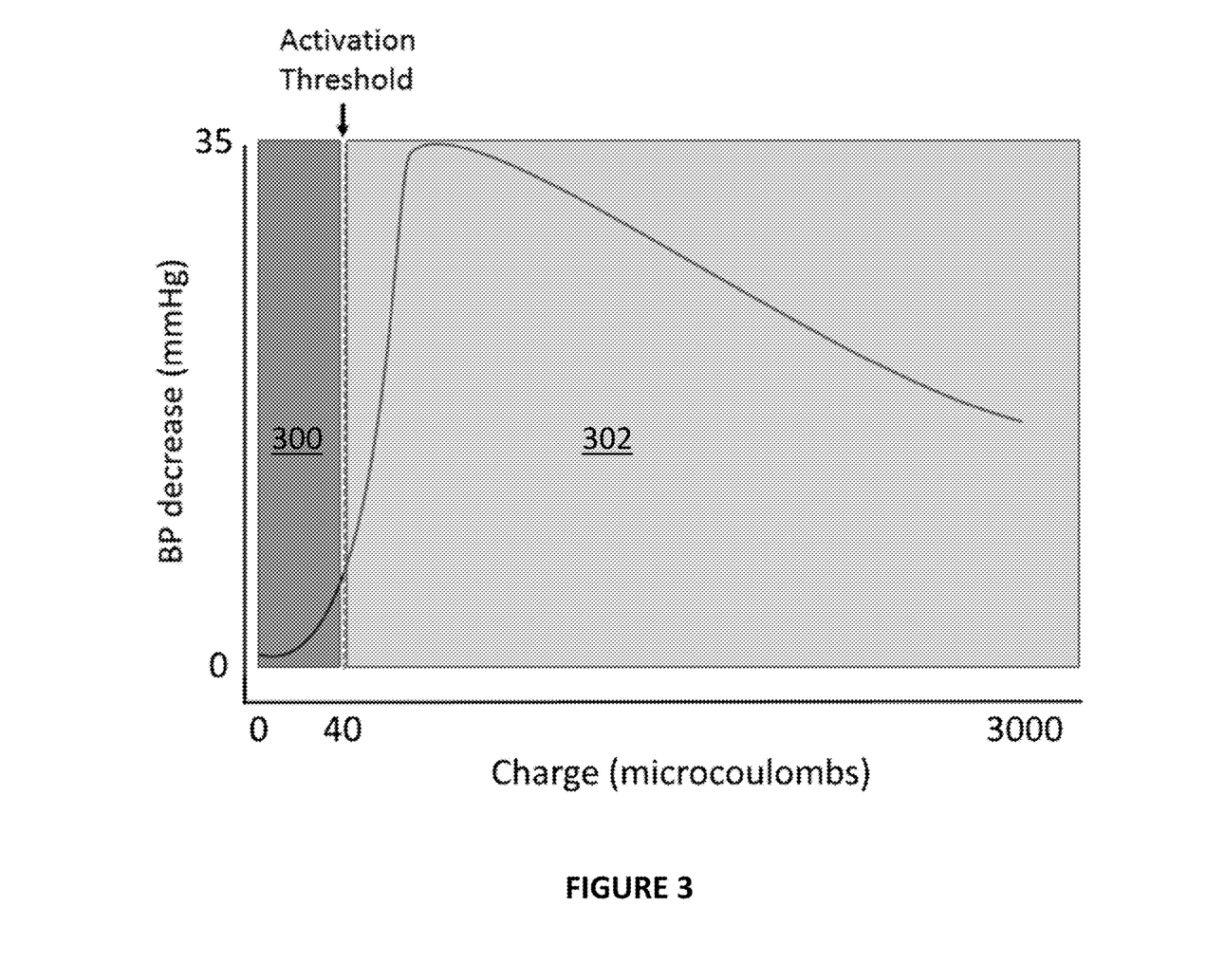
FIG. 3 illustrates the relationship between blood pressure decrease and total non-invasive auriculotemporal nerve stimulation charge.

FIG. 3 illustrates the relationship between blood pressure decrease and total atNS current (shown as charge in microcoulombs). In other words, FIG. 3 illustrates the relationship between applied charge and the effect of the stimulation on decreasing blood pressure. As seen in the figure, blood pressure decrease begins at an 'activation threshold' charge during atNS of about 40 microcoulombs and maximum blood pressure decrease due to atNS occurs at about 70 microcoulombs. Thereafter, the atNS effect on decreasing blood pressure diminishes, but remains significant relative to the decrease caused by the activation threshold charge. Accordingly, the region 300 to the left of the activation threshold corresponds to a "below threshold" charge insufficient to decrease blood pressure, while the region 302 to the right of the activation threshold corresponds to an "above threshold" charge that can effectuate blood pressure decrease.

Depending on the embodiment, atNS stimulation protocols may control any stimulation parameter to achieve above threshold charges. For example, an applied current, frequency, pulse width, pulse train duration, and waveform may all be selectively controlled to achieve a desired stimulation charge for the unique features of an individual patient and desired blood pressure control. Such changes in stimulation parameters may be constrained for example by the ability to apply stimulation at a particular location on a patient's ear, the patient's particular bioimpedance (e.g., as affected by fat and water concentrations in the body), and the unique variations in anatomical innervation of each patient's ear.

In view of this, atNS stimulation at less than or equal to about 3 mA, at less than or equal to about 100 Hz, with a pulse width less than or equal to about 0.9 ms (900 µs), for a pulse train less than or equal to 15 minutes can effectuate a desired blood pressure decrease without corresponding decreases in heart and breathing rate. More particularly, atNS may be applied at about 0.4-1.6 mA, at less than or equal to 60 Hz, with a 0.3 ms (300 μs) pulse width, and a 0.5-30 second train to supply a desired above threshold charge to effectuate selective blood pressure decrease. According to one particular stimulation protocol embodiment, atNS is applied at about 1.6 mA at 5 Hz, having a 300 μs pulse width for a 30 second train duration. Such stimulation may be applied according to any wave type, for example, a biphasic square wave having an anodal leading edge. Further, although particular train durations are noted above, atNS may applied for any period of time for which a blood pressure change is desired, for example, during an entire period of a hypertensive event, which may last many minutes.

The above-discussed non-invasive stimulation may be performed with dry electrodes or hydrogel electrodes. The dry electrodes may be comprised of a mixed ionic electronic conducting (MIEC) electrode interface material, such as that described in International Publication Number WO 2018/191317, published Oct. 18, 2018 and entitled "MIXED IONIC ELECTRONIC CONDUCTORS FOR IMPROVED CHARGE TRANSPORT IN ELECTROTHERAPEUTIC DEVICES," and which is herein incorporated by reference. Such MIEC materials comprise a flexible elastic material that is light weight and can be easily molded to fit several form factors and interface geometries. This allows for personalized bioelectronic interfaces to mold to specific body parts of a patient (such as the outer ear), and for enhanced patient comfort and electrode adherence. Additionally, the MIEC material robustly electrically couples to the skin. The MIEC interface can use carbon nanotubes as the electronic conductor and hyaluronic acid as the ionic conductor interspersed in a matrix. This allows for low interfacial resistances and efficient flow of current from a traditional metallic interface, to the MIEC, and through the skin for stimulation. Still further, the MIEC interface prevents the need for a hydrogel or conductive lotion, and is robust to temperature and humidity fluctuations. Considering the above, electrodes incorporating MIEC interface materials can enable access to larger patient populations for maximizing the application of bioelectronic medicines, such as atNS, to patients suffering from disease.

Figure 4:
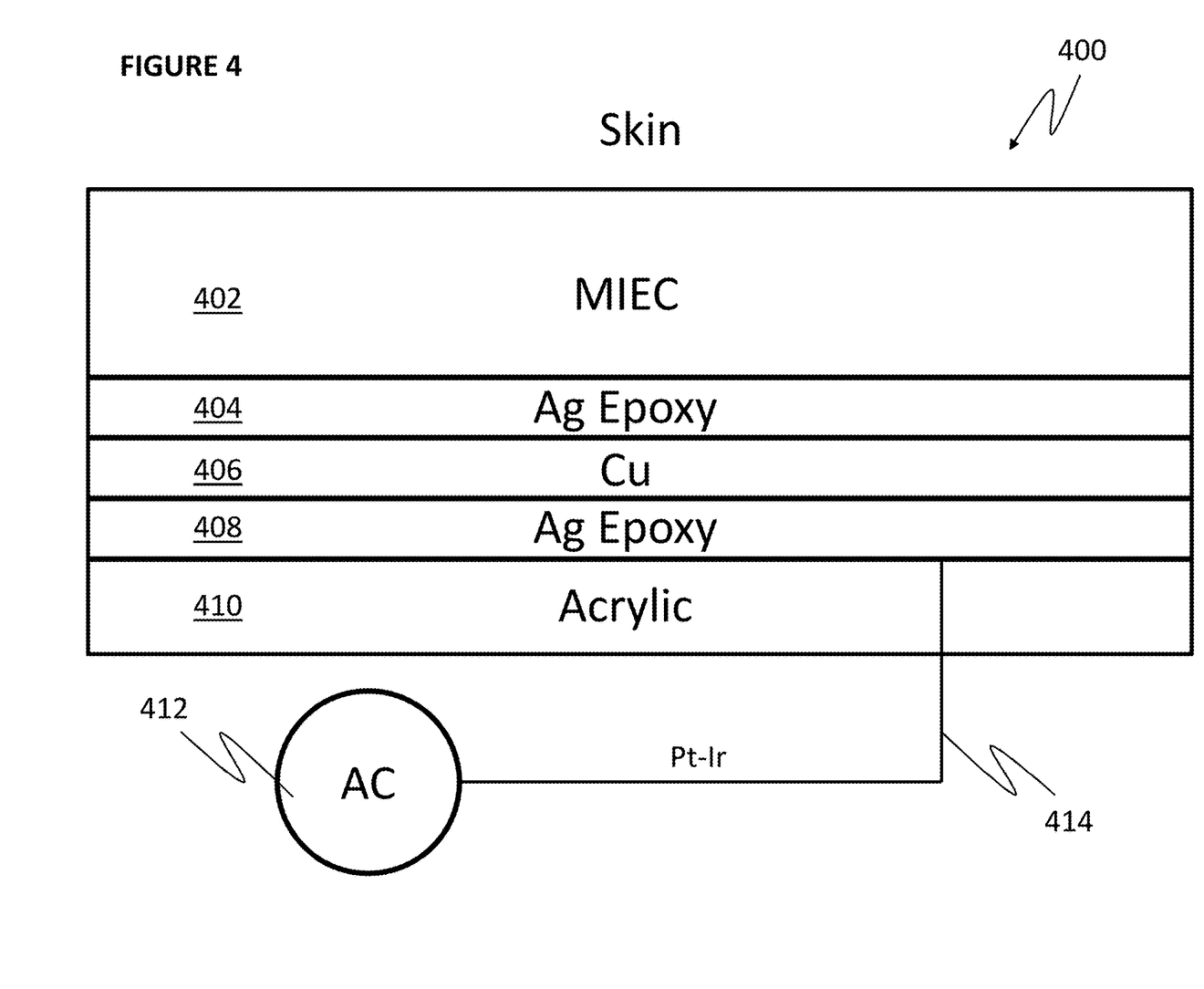
FIG. 4 illustrates an example mixed ionic electronic conducting (MIEC) electrode.

According to one embodiment, such MIEC interfaces are comprised of a mixture of carbon nanotubes (CNTs), hyaluronic acid (HA), and elastomeric particles (AN-BD particles). FIG. 4 illustrates an example dry electrode utilizing an MIEC interface. As seen therein, the electrode 400 is comprised of traditional conducting layers attached to stimulation wires and a computer-controlled stimulator. In the particular embodiment of FIG. 4, these conducting layers include a copper (Cu) layer 406 and acrylic layer 410 bonded by silver (Ag) epoxy layers 404, 408. The silver epoxy layer 408 between the copper and acrylic layers 406, 410 is supplied with an alternating current (AC) voltage or like stimulation current (e.g., according to the stimulation parameters/protocol) from a power source 412 via a platinum iridium (Pt—Ir) conductor 414. The silver epoxy layer 404 bonds the MIEC interface layer 402 to the copper layer 406. The electrode 400 is preferably configured to be attachable to the ear (e.g., via a clip or conducting biocompatible adhesive) in a manner that renders it capable of applying stimulation to the auriculotemporal or other desired nerves.

In one embodiment, the power source 412 provides the AC voltage or stimulation current from a current source (e.g., a bipolar current stimulator) or via capacitive discharge. The source 412 may be controlled by a controller, such as an integrated circuit, processor, discrete circuit, or the like (not shown), that controls the output of the source 412 according to stimulation parameters and/or protocol such as those discussed above. In some embodiments, these parameters may be predetermined and stored in a memory.

In some embodiments, the power source 412, controller, and resulting atNS stimulation may be part of a closed-loop stimulation system. Such a closed-loop system could include various sensors for monitoring and/or predicting a hypertensive crisis, physiological state, or the like, for example, based on a monitored blood pressure, heart rate, photoplethysmogram, and/or other physiological parameters. Such measurements may be taken by any known means, for example, photoplethysmography, electrocardiograms (ECG), and the like. The controller may receive signals indicating such physiological parameters of a patient and determine whether the crises or condition is occurring or has ended, or predict whether the condition is about to occur or is about to end. Based on these determinations, the controller may identify proper stimulation protocols and parameters, and timing of stimulation, and then control the power source to supply the corresponding atNS stimulation. The proper stimulation protocols and parameters may be based on the patient's current condition (e.g., a severity of the condition), predicted future condition, and/or be timed to coincide with various physiological events e.g., a particular portion of the cardiac cycle, such as the R-wave). These determinations and predictions may be based on the measured parameters may be dependent on 'past' information in a time series (e.g., a long short-term memory model) or independent of 'past' information (e.g., instantaneous predictions from a support vector machine). In some embodiments the controller may include machine learning models or be part of a machine learning system trained to determine for example when (e.g., in which physiological states) and how (e.g., particular protocols) to effect stimulation.

For example, with the above-described closed-loop stimulation, atNS could be performed before a high blood pressure reading for preventative purposes. In another example, stimulation could be performed during a high blood pressure reading in order to lower blood pressure. In still another example, stimulation could be performed after a high blood pressure reading in order to facilitate recovery—for example because high blood pressure events can cause target organ damage, damaged tissue may benefit from increased blood perfusion/flow for delivery of nutrients, oxygen, and/or immune factors that can accelerate tissue healing.

Figure 5A:
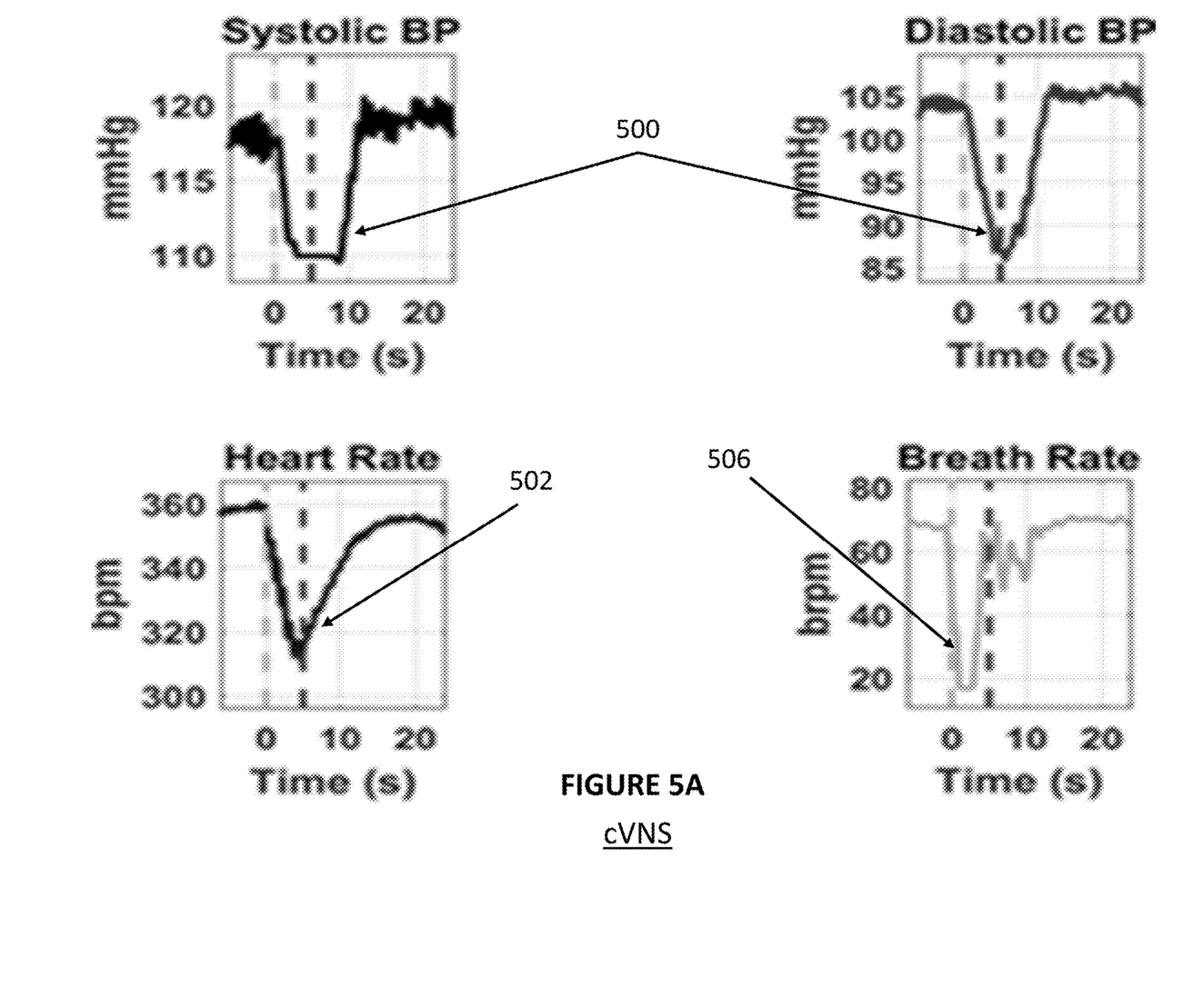
FIGS. 5A and 5B illustrate physiological parameters resulting from left cervical Vagus nerve stimulation (cVNS) and non-invasive auriculotemporal nerve stimulation (atNS), respectively, according to a first experiment.
Figure 5B:
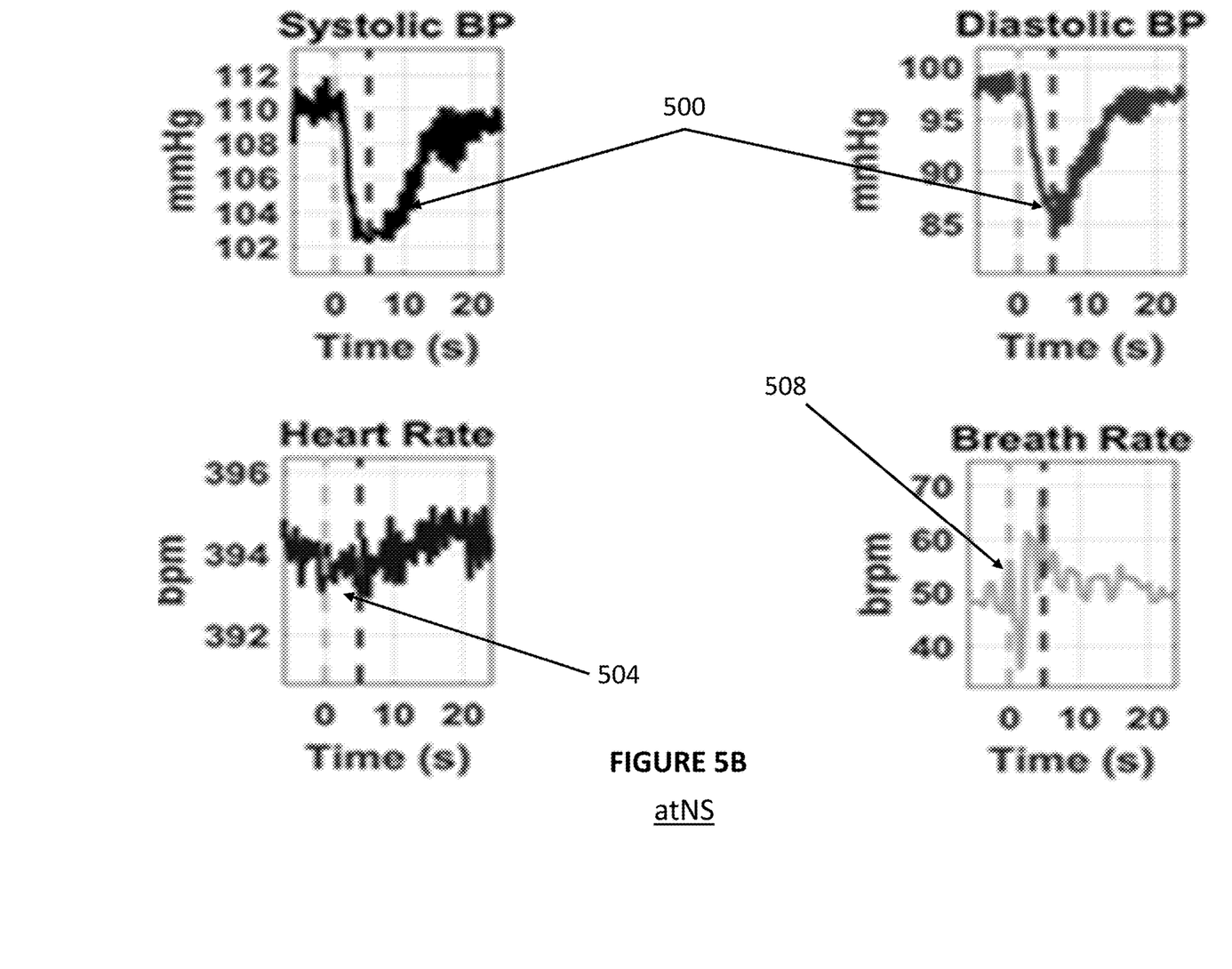
Figure 6A:
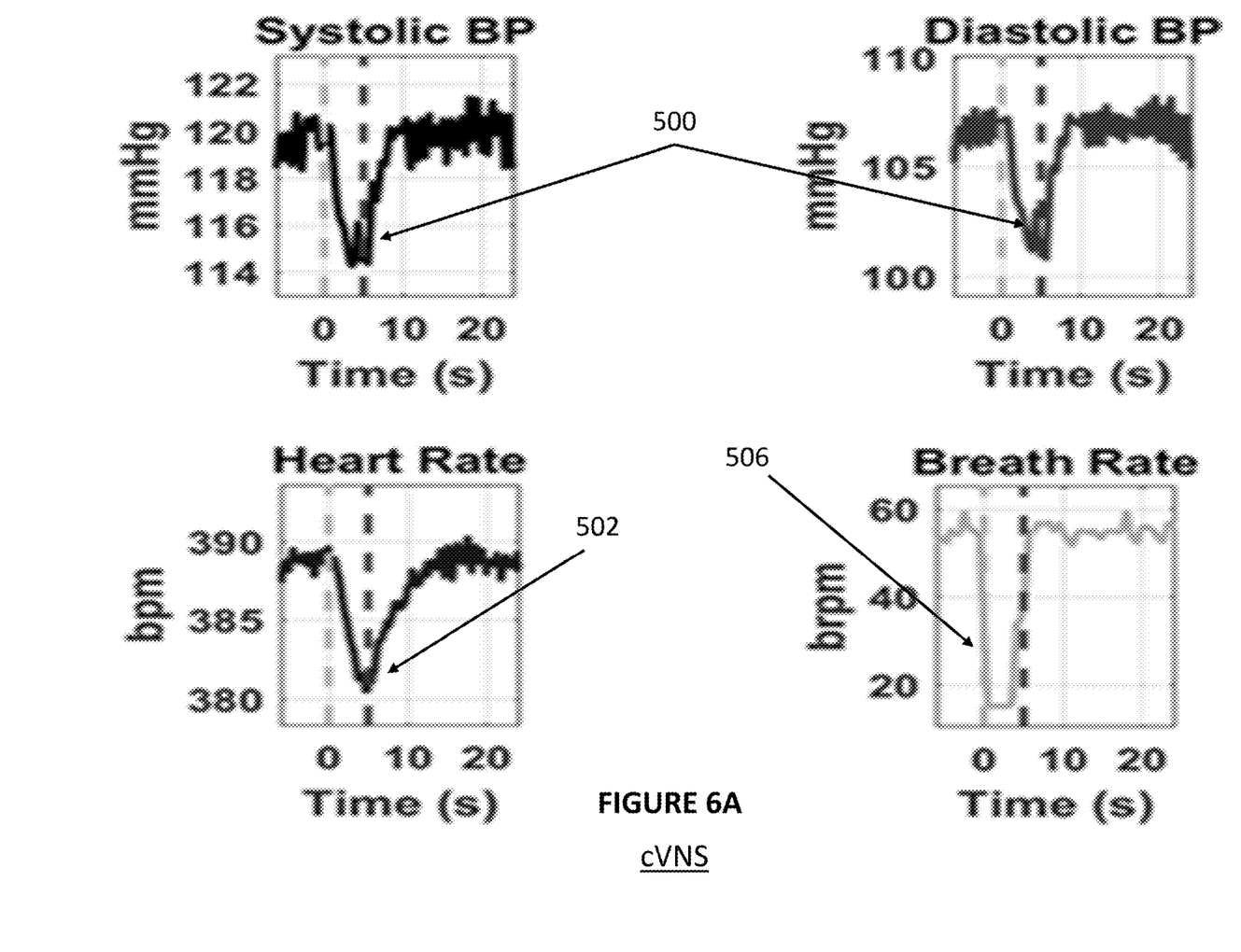
FIGS. 6A and 6B illustrate physiological parameters resulting from left cervical Vagus nerve stimulation (cVNS) and non-invasive auriculotemporal nerve stimulation (atNS), respectively, according to a second experiment.
Figure 6B:
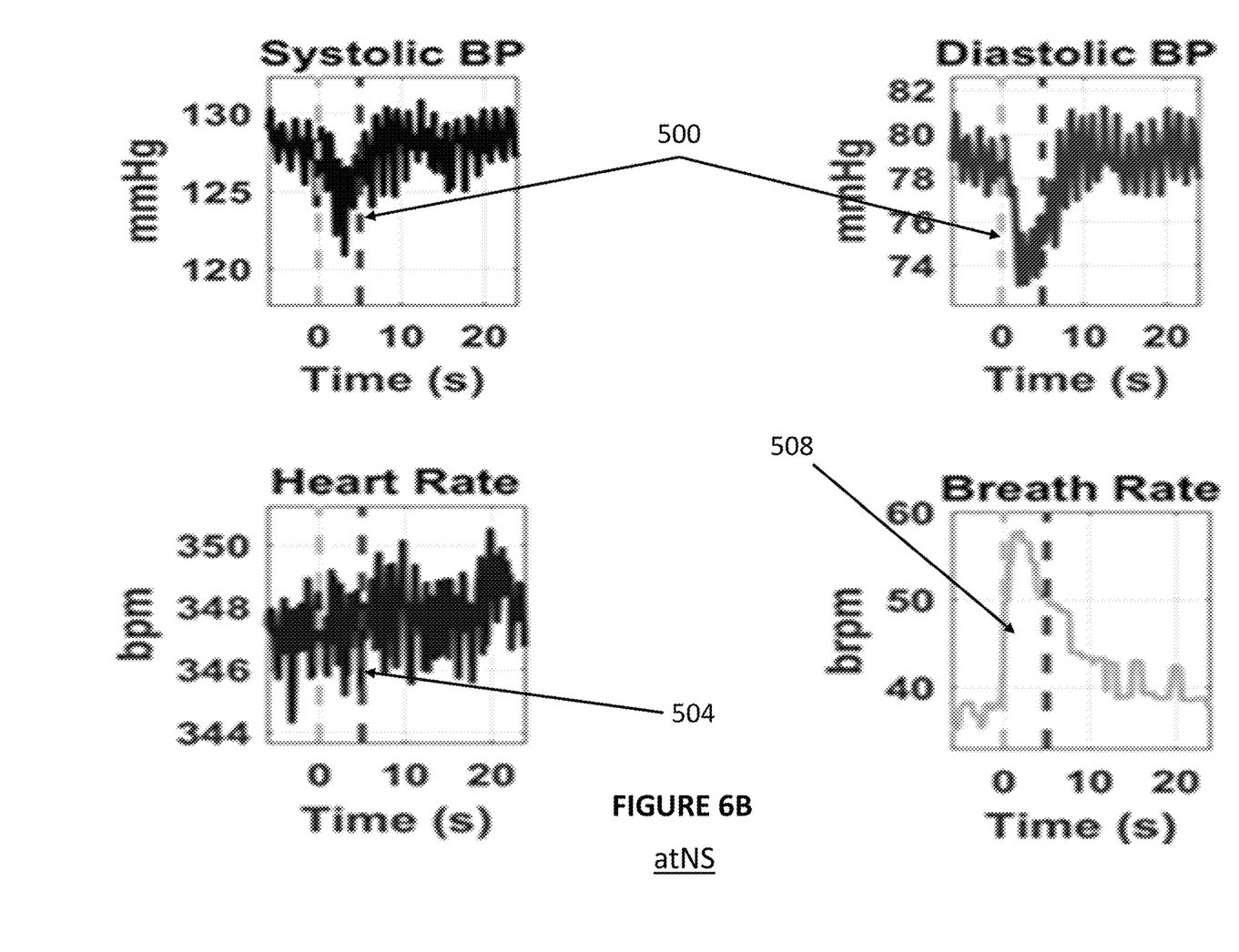

The above-described atNS has been shown experimentally in rats. In those experiments, several anesthetized in-vivo recordings were taken in adult female Sprague Dawley rats. The animals were deeply anesthetized with Isoflurane (via inhalation) and given Carprofen (via injection). An electrocardiogram (ECG, EMKA), right carotid arterial blood pressure, and photoplethysogram were taken during the experiment. The left cervical vagus nerve was surgically isolated and interfaced with a platinum iridium (Pt—Ir) bipolar cuff. In the same animal, the left auriculotemporal nerve was interfaced with an MIEC bipolar electrode on the surface of the skin on the outer ear. Left cervical Vagus nerve stimulation (cVNS) via the Pt—Ir bipolar cuff was used as a control to illustrate cardiopulmonary effects accompanied by well-known side effects (e.g. bradycardia & bradypnea, as noted above). Non-invasive auriculotemporal nerve stimulation with the MIEC electrode at the ear was used as a comparator, demonstrating the above-described 'selective' blood pressure decreases without significant side effects (e.g., bradycardia and bradypnea) observed. Both the cVNS and atNS were applied with common stimulation parameters. Results from these experiments are illustrated in FIGS. 5A and 5B, 6A and 6B, and 7A and 7B. Each figure illustrates systolic blood pressure, diastolic blood pressure, heart rate, and breath rate measured over the length of the experiment FIG. 5A illustrates the above-mentioned recorded physiological parameters resulting from cVNS according to a first experiment, and FIG. 5B illustrates those physiological parameters resulting from atNS according to the first experiment. In the first experiment shown in FIGS. 5A and 5B, a 1.6 mA stimulation was applied at 30 Hz with a 300 μs pulse width for a 5 second train. The dashed lines indicate the stimulation period. Similarly, FIGS. 6A and 6B illustrate recorded physiological parameters from cVNS and atNS, respectively, according to a second experiment. The second experiment shown in FIGS. 6A and 6B applied a stimulation of 1.0 mA at 30 Hz with a 300 μs pulse width for a 5 second train. As noted above, the stimulation protocols for the first and second experiments are above threshold protocols capable of evoking a decrease in blood pressure.

As can be seen in each of FIGS. 5A and 5B, and 6A and 6B, the above threshold stimulation evoked both a systolic and diastolic a blood pressure decrease, identified in each graph by reference numeral 500. However, comparing FIG. 5A to FIG. 5B, and 6A to 6B (i.e., comparing cVNS to atNS stimulation), the decrease in blood pressure 500 was accompanied by a concomitant decrease in heart rate with cVNS 502 as shown in FIGS. 5A and 6A. In contrast, heart rate remained steady or increased 504 during atNS application as seen in FIGS. 5B and 6B. Similarly, cVNS was accompanied by a clear drop in breathing rate 506, evident in both FIGS. 5A and 5B. While some change in breathing rate 508 during atNS is noticeable in FIGS. 5B (a quick decrease followed by increase) and 6B (an increase), the breathing rate began returning to steady state prior to removal of the stimulation in both experiments.

Figure 7A:
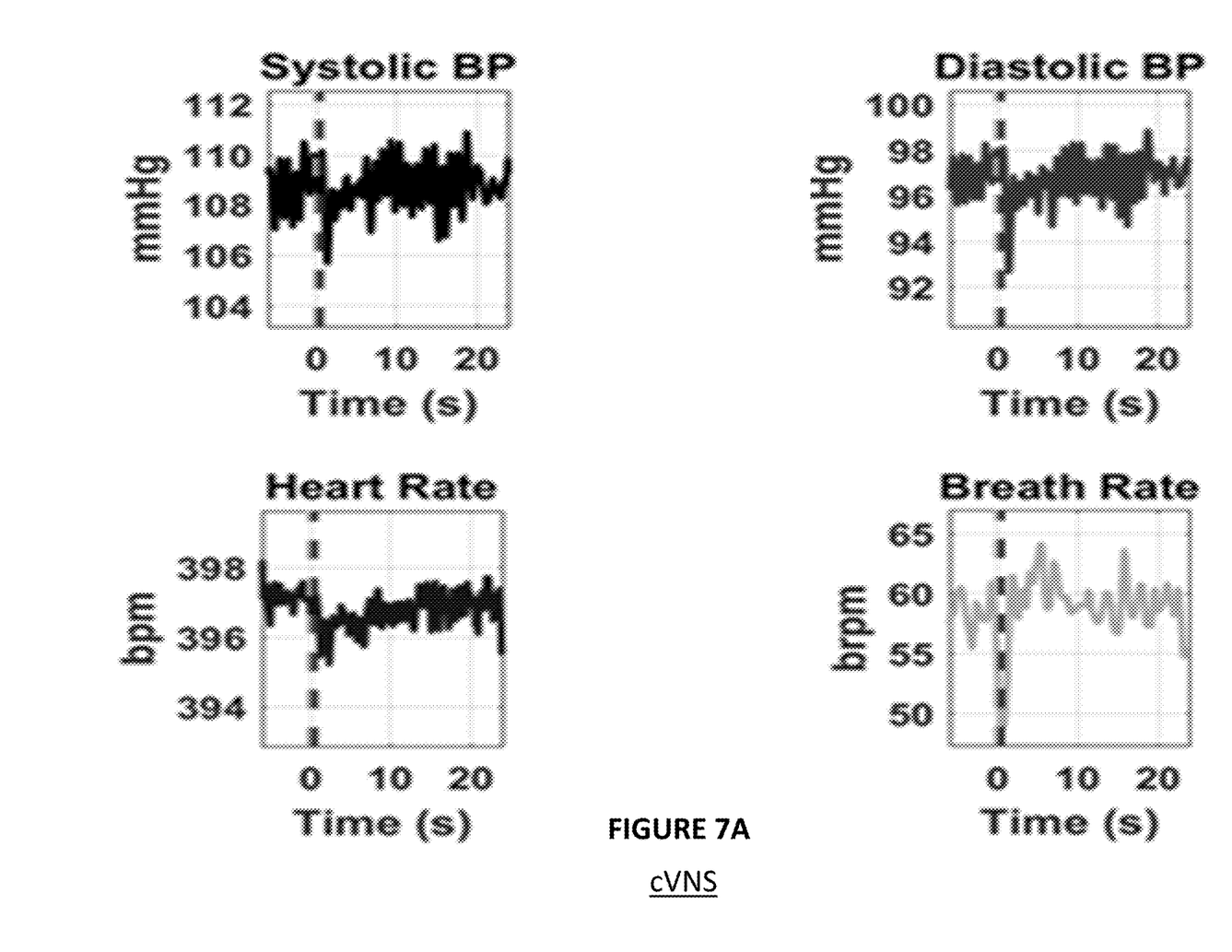
FIGS. 7A and 7B illustrate physiological parameters resulting from left cervical Vagus nerve stimulation (cVNS) and non-invasive auriculotemporal nerve stimulation (atNS), respectively, according to a third experiment.
Figure 7B:
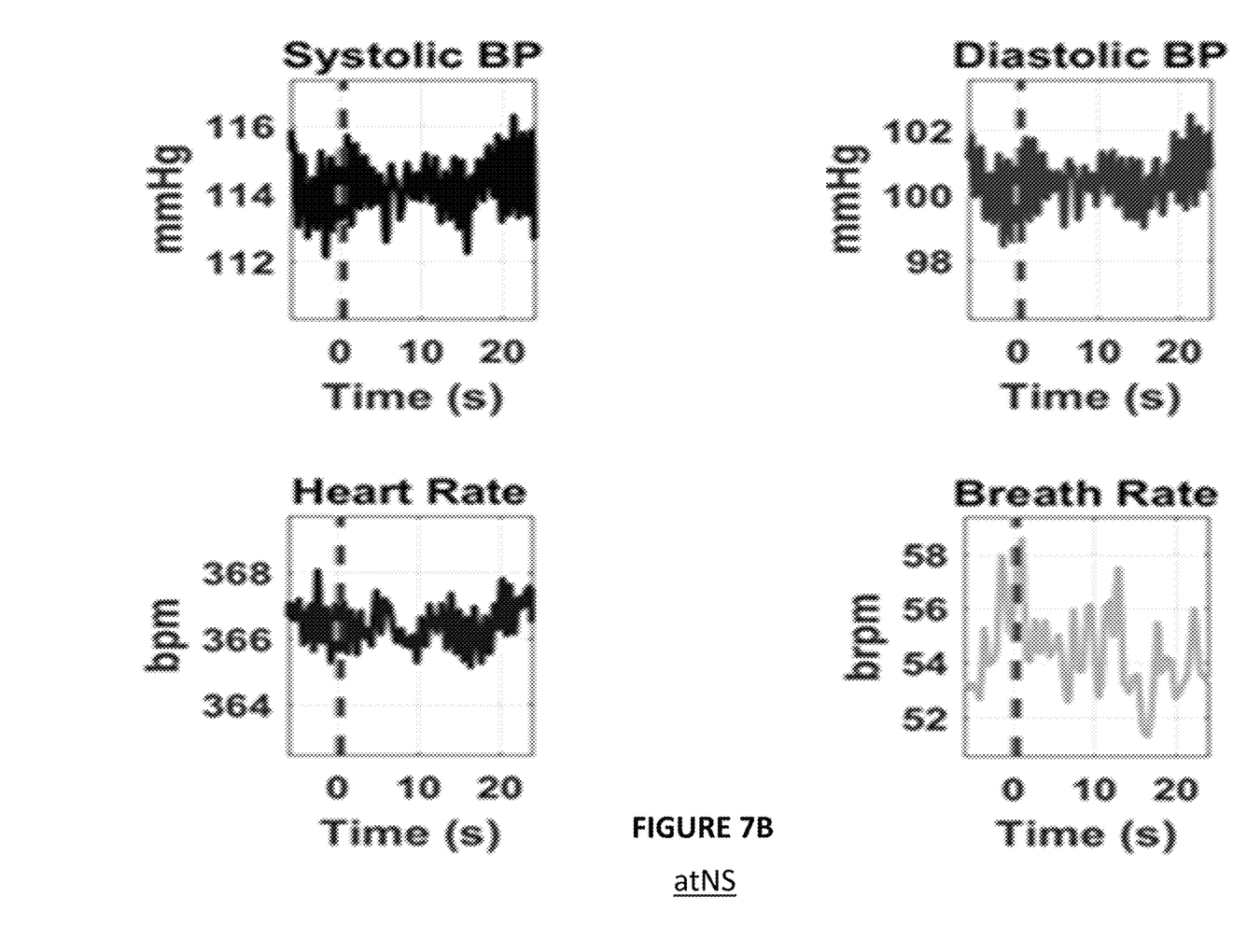

FIGS. 7A and 7B illustrate results of a third experiment in which a below threshold stimulation protocol of 0.4 mA was applied at 60 Hz with a 300 μs pulse width for a 0.5 second train was applied as a control. As seen cVNS (FIG. 7A) and atNS (FIG. 7B) evoked little to no modulation of cardiopulmonary physiology. In each case, each of the four measured parameters (systolic blood pressure, diastolic blood pressure, heart rate, and breath rate) remained essentially unchanged during and after the stimulation period.

Figure 8A:
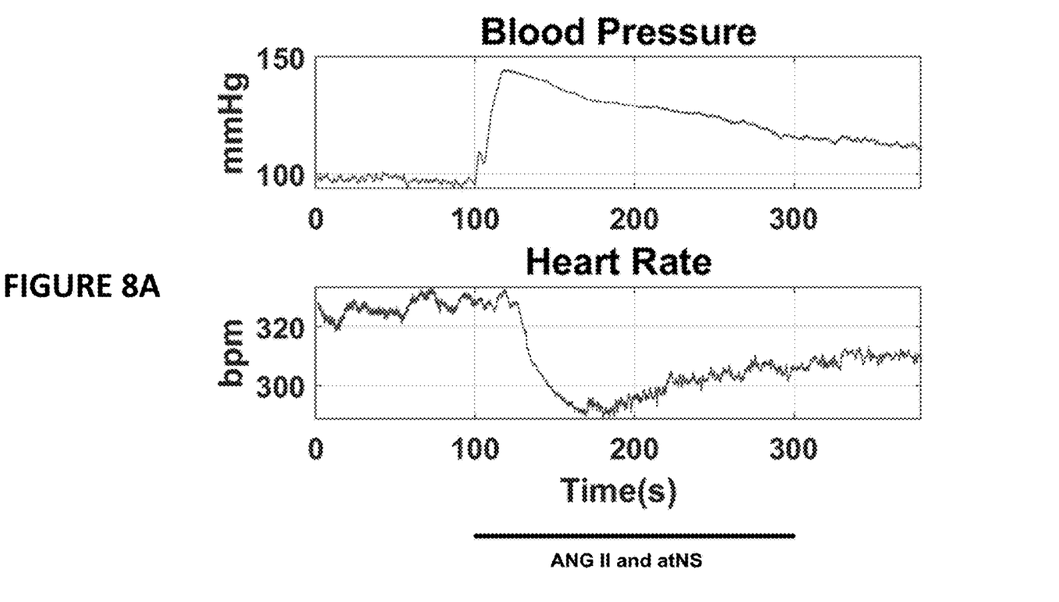
FIGS. 8A and 8B illustrate physiological parameters during a hypertensive crisis with and without auriculotemporal nerve stimulation (atNS), respectively, according to a fourth experiment.
Figure 8B:
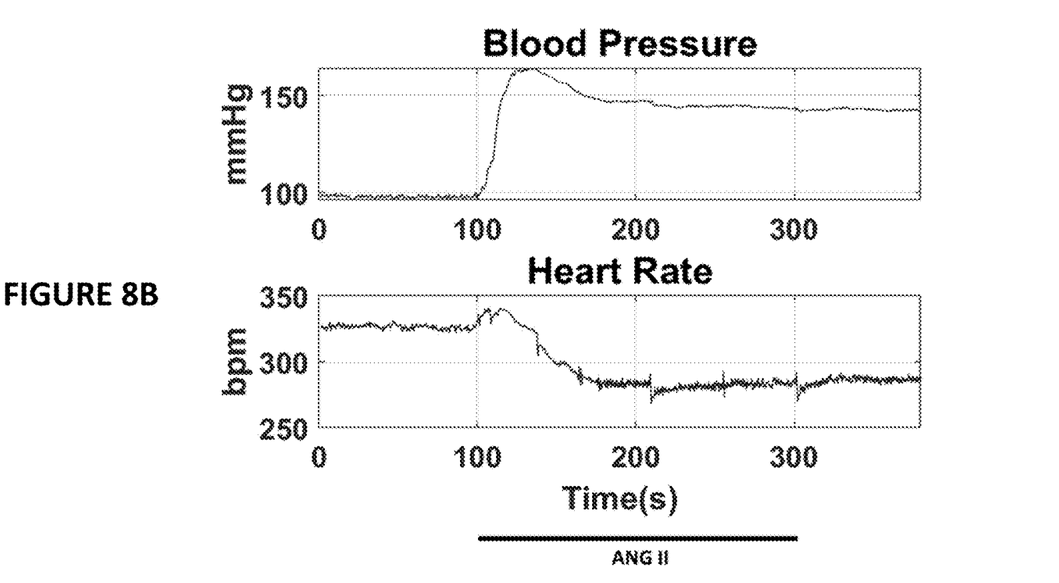

Another experiment, illustrated in FIGS. 8A and 8B, further demonstrates the effects of atNS during a hypertensive crisis. In these experiments, rats were anesthetized, similar to the approach described above (with Isoflurane and Carprofen). Ang II was introduced to the animal's circulatory system via a tail vein i.v. line. A syringe pump controlled the infusion rate of the Ang II into the animal, thereby controlling the induction of a hypertensive crisis. In one case (FIG. 8A), atNS was applied to the left auriculotemporal nerve interfaced with a mixed ionic electronic conducting bipolar electrode on the surface of the skin on the outer ear simultaneously with the Ang II. In a comparative case (FIG. 8B), no stimulation was applied in order to determine the hypertensive affect caused by the Ang II.

In each case, blood pressure and heart rate were monitored for a period of 400 seconds. Ang II (and atNS) was applied for 200 seconds (between 100 and 300 seconds). Prior to application of Ang II, the resting level of blood pressure was about 100 mmHG and the resting level of the heart rate was about 325 bpm. As seen in FIG. 8A, Ang II caused blood pressure to increase almost to 150 mmHG, and heart rate to decrease to less than 325 bpm. However, after roughly 20 seconds, blood pressure began to decrease continually towards the resting level, reaching about 120 mmHG by the end of Ang II application and stimulation. Similarly, after about a minute of applied stimulation the heart rate began to increase towards its resting level, reaching a steady state of about 310 bpm by the end of Ang II application and stimulation. In short, the increase in heart rate occurred concomitantly with the decrease in blood pressure.

FIG. 8B illustrates the hypertensive effects of Ang II application without stimulation. In contrast to the stimulation case illustrated in FIG. 8A, blood pressure increased to about 160 mmHG, and reached a steady state of about 150 mmHG throughout the remainder of the experiment. Similarly, blood pressure decreased to a steady state of about 275 bpm throughout the experiment. More particularly, the decrease in heart rate temporally corresponded with the change in blood pressure. That is, heart rate and blood pressure both began to change at the beginning of Ang II application, and reached steady state at about the same time.

Comparing the blood pressures and heart rates in each instance, atNS mitigated the maximum natural increase in blood pressure (limiting the increase to a maximum less than 150 mmHG), and nearly caused it to return to a resting level within the 200 seconds of application. Similarly, the natural bradycardia was mitigated, not exacerbated by the stimulation. In other words, the experiment of FIGS. 8A and 8B demonstrates that atNS is able to mediate "selective" blood pressure reduction during an induced hypertensive event.

According to the present disclosure, noninvasive stimulation of the auriculotemporal nerve (on the surface of the ear) facilitates a decrease in blood pressure without a corresponding decrease in heart rate or breathing rate, as occurs in stimulation of the cervical vagus and trigeminal nerves. Such a therapy may be particularly beneficial during hypertensive crises where the body naturally decreases heart rate and breathing rate to compensate for an increased blood pressure.

While the above stimulation has been described particularly as it relates to auriculotemporal nerve on the left ear, it is to be understood that the principles described herein may be equally applicable to the right ear. Furthermore, due to the density of different nerve branches within the ear, indirect stimulation of nerves other than auriculotemporal nerve (e.g., by fields produced by the stimulation electrode) may contribute to the above-described effects. Similarly, this means that a stimulation electrode need not necessarily be placed on the ear in a manner that primarily or only stimulates the auriculotemporal nerve. Rather, general placement of the electrode on the surface of the outer ear may be sufficient to evoke the above described responses.

What I claim is:

1. A method comprising non-invasively stimulating a surface of an outer ear or an auriculotemporal nerve of a subject such that:
   a blood pressure of the subject decreases relative to the blood pressure at the time stimulation is applied; and
   concomitantly with the decrease in blood pressure: a heart rate of the subject is maintained or increased, or the heart rate of the subject increases more than in response to said stimulation applied to the cervical vagus or trigeminal nerve.

2. The method of claim 1, wherein the stimulation is applied at an area of the outer ear innervated by the auriculotemporal nerve of the subject.

3. The method of claim 1, wherein the stimulation is applied with an electrode comprising a mixed ionic electronic conducting electrode interface.

4. The method of claim 1, wherein the applied stimulation is of at least 40 microcoulombs.

5. The method of claim 1, wherein the applied stimulation comprises pulses of less than or equal to 3 mA at less than or equal to 100 Hz, each pulse having a pulse width less than or equal to 0.9 ms for a pulse train less than or equal to 15 minutes.

6. The method of claim 5, wherein each pulse is a biphasic square wave having an anodal leading edge.

7. The method of claim 1, wherein the stimulation is applied during a hypertensive crisis.

8. The method of claim 1, wherein a parameter of the stimulation or a time of application of the stimulation is determined based on a detected physiological parameter.

9. A method of decreasing a blood pressure of a subject comprising stimulating a surface of an outer ear or an auriculotemporal nerve of a subject with at least 40 microcoulombs, thereby concomitantly decreasing said blood pressure and maintaining or increasing a heart rate of said subject during said stimulation.

10. The method of claim 9, wherein the stimulation is applied at an area of the outer ear innervated by the auriculotemporal nerve of the subject.

11. The method of claim 9, wherein the stimulation is applied with an electrode comprising a mixed ionic electronic conducting electrode interface.

12. The method of claim 9, wherein the stimulation comprises electrical pulses of less than or equal to 3 mA at less than or equal to 100 Hz, each pulse having a pulse width less than or equal to 0.9 ms for a pulse train less than or equal to 15 minutes.

13. The method of claim 12, wherein each pulse is a biphasic square wave having an anodal leading edge.

14. The method of claim 9, wherein a parameter of the stimulation or a time of application of the stimulation is determined based on a detected physiological parameter.

15. A stimulation device comprising:
a power source; and
an electrode configured to apply a stimulation current to a surface of an outer ear of a subject, the stimulation current being supplied by the power source, wherein:
the stimulation current applies at least 40 microcoulombs, and
a blood pressure of the subject is decreased concomitantly with a maintenance or increase in a heart rate of the subject, in response to said application of the stimulation current.

16. The stimulation device of claim 15, wherein the stimulation current comprises pulses of less than or equal to 3 mA at less than or equal to 100 Hz, each pulse having a pulse width less than or equal to 0.9 ms for a pulse train less than or equal to 15 minutes.

17. The stimulation device of claim 16, wherein each pulse is a biphasic square wave having an anodal leading edge.

18. The stimulation device of claim 15, wherein the electrode comprises a mixed ionic electronic conducting electrode interface.

19. The stimulation device of claim 15, further comprising:
a controller; and
a physiological sensor configured to detect a physiological parameter of the subject,
wherein the controller is configured to determine a parameter of the stimulation current or a time of application of the stimulation current, and to correspondingly control the power source to supply the stimulation current to the electrode, based on the detected physiological parameter.

20. The stimulation device of claim 19, wherein the controller is configured to cause said application of the stimulation current during a hypertensive crisis.

* * * * *